US011116738B2

(12) United States Patent
Wu

(10) Patent No.: US 11,116,738 B2
(45) Date of Patent: Sep. 14, 2021

(54) METHODS FOR TREATING NEUTROPENIA USING RETINOID AGONISTS

(71) Applicant: CHILDREN'S HOSPITAL LOS ANGELES, Los Angeles, CA (US)

(72) Inventor: Lingtao Wu, Rancho Palos Verdes, CA (US)

(73) Assignee: CHILDREN'S HOSPITAL LOS ANGELES, Los Angeles, CA (US)

(*) Notice: Subject to any disclaimer, the term of this patent is extended or adjusted under 35 U.S.C. 154(b) by 0 days.

(21) Appl. No.: 14/405,141

(22) PCT Filed: Jun. 7, 2013

(86) PCT No.: PCT/US2013/044828
§ 371 (c)(1),
(2) Date: Dec. 2, 2014

(87) PCT Pub. No.: WO2013/185105
PCT Pub. Date: Dec. 12, 2013

(65) Prior Publication Data
US 2015/0164836 A1 Jun. 18, 2015

Related U.S. Application Data

(60) Provisional application No. 61/656,815, filed on Jun. 7, 2012.

(51) Int. Cl.
*A61K 31/196* (2006.01)
*A61K 45/06* (2006.01)
*A61K 31/192* (2006.01)

(52) U.S. Cl.
CPC .......... *A61K 31/196* (2013.01); *A61K 31/192* (2013.01); *A61K 45/06* (2013.01)

(58) Field of Classification Search
None
See application file for complete search history.

(56) References Cited

U.S. PATENT DOCUMENTS

| 5,700,650 A | 12/1997 | Mak et al. |
| 10,286,039 B2 | 5/2019 | Wu |

(Continued)

FOREIGN PATENT DOCUMENTS

| CN | 1816345 A | 8/2006 |
| EA | 201101035 A1 | 2/2012 |

(Continued)

OTHER PUBLICATIONS

Tohda, The effects of retinoic acid analogues on the blast cells of acute myeloblastic leukemia in culture, Int. J. of Oncology, 1994, 4, pp. 1311-1314.*

(Continued)

*Primary Examiner* — Savitha M Rao
*Assistant Examiner* — Andrew P Lee
(74) *Attorney, Agent, or Firm* — Nixon Peabody LLP; Linda B. Huber; Suwei Zhu

(57) ABSTRACT

The invention provides methods for treating neutropenia in a subject in need thereof comprising providing a composition comprising a retinoid agonist and administering an effective amount of the composition to the subject to treat (Continued)

neutropenia, thereby treating neutropenia to the subject in need thereof.

16 Claims, 10 Drawing Sheets

(56) References Cited

U.S. PATENT DOCUMENTS

| | | | |
|---|---|---|---|
| 2005/0003453 | A1 | 1/2005 | Sarkar et al. |
| 2009/0176862 | A1 | 7/2009 | Chandraratna et al. |
| 2011/0052574 | A1* | 3/2011 | Dick .................. A61K 39/3955 424/133.1 |
| 2012/0201884 | A1 | 8/2012 | Gokaraju et al. |
| 2013/0165637 | A1 | 6/2013 | Yan et al. |
| 2014/0037600 | A1 | 2/2014 | Yu et al. |
| 2017/0007671 | A1 | 1/2017 | Wu |

FOREIGN PATENT DOCUMENTS

| | | |
|---|---|---|
| EP | 1632241 A1 | 3/2006 |
| EP | 2143428 A1 | 1/2010 |
| EP | 2858636 B1 | 9/2018 |
| HK | 1208630 B | 9/2019 |
| ID | 2017/10358 | 9/2017 |
| IN | 201617026587 A | 8/2016 |
| JP | 2001-506998 A | 5/2001 |
| RU | 2007124325 A | 1/2009 |
| RU | 2008142899 A | 5/2010 |
| WO | 9724116 A2 | 7/1997 |
| WO | 2004100972 A1 | 11/2004 |
| WO | WO 2006010503 | 2/2006 |
| WO | WO2006020891 | 2/2006 |
| WO | 2006071451 A2 | 7/2006 |
| WO | 2010/028388 A1 | 3/2010 |
| WO | 2013169864 A2 | 11/2013 |
| WO | 2013/186105 A1 | 12/2013 |
| WO | WO 2013185105 | 12/2013 |
| WO | 2015126989 A1 | 8/2015 |
| ZA | 2016/05109 B | 9/2017 |

OTHER PUBLICATIONS

Visser, Neutropenia, neutrophil dysfunction, and inflammatory bowel disease in glycogen storage disease type lb: Results of the European Study on Glycogen Storage Disease Type I, Journal of Pediatrics, 2000, 137 (2), pp. 187-191.*
Shibakura, A Retinoic Acid Receptor-a (RARa) Selective Agonist Modulates Procoagulant Activity of Acute Promyelocytic Cells and Induces Their Differentiation Into Neutrophils, Blood, 1998, 91(2), pp. 724-728.*
Tobita, Treatment with a New Synthetic Retinoid, Am80, of Acute Promyelocytic Leukemia Relapsed From Complete Remission Induced by All-trans Retinoic Acid, Blood, 1997, 90(3), pp. 967-973.*
Naina, Successful Treatment of Relapsed and Refractory Extramedullary Acute Promyelocytic Leukemia with Tamibarotene, Journal of Clinical Oncology, 2011,29(18), pp. e534-e536.*
Huston, Agents under investigation for the treatment and prevention of neutropenia, Expert Opin. Investig. Drugs, 2007, 16(11), pp. 1831-1840.*
Welte, Pathophysiology and treatment of severe chronic neutropenia, Ann Hematol, 1996, 72, pp. 158-165. (Year: 1996).*
Cullen, Antibacterial Prophylaxis after Chemotherapy for Solid Tumors and Lymphomas, New England Journal of Medicine, 2005, 353(10), pp. 988-998. (Year: 2005).*
Skubitz, CD66a, CD66b, CD66c, and CD66d each independently stimulate neutrophils, Journal or Leukoeyte Biology, 1996, 60, pp. 106-117. (Year: 1996).*
Mosteller RD. Simplified calculation of body-surface area. N Engl J Med 1987;317:1098. (Year: 1987).*
PCT/US2013/044828 Written Opinion dated Nov. 8, 2013; 4 pages.
PCT/US2013/044828 International Preliminary Report on Patentability dated Dec. 9, 2014; 5 pages.
ISR for PCT/US2013/044828, 2 pages.
European Application No. 138800873.5 Extended Search Report dated May 2, 2016; 14 pages.
Schon et al. A comparative study of three methods to evaluate an intervention to improve empirical antibiotic therapy for acute bacterial infections in hospitalized patients. Scandinavian Journal of Infectious Diseases (2011). 43:251-257.
European Application No. 138800873.5 Partial Supplementary Search Report dated Dec. 4, 2015; 8 pages.
Kagechika et al. Retinobenzoic Acids. Structure-Activity Relationships of Aromatic Amids with Retinoidal Activity. Journal of Medicinal Chemistry (1988). 31(11)2182-2192.
Uruno et al. All-trans retinoic acid and a novel synthetic retinoid tamibarotene (Am80) differentially regulate CD38 expression in human leukemia HL60 cells: possible involvement of protein kinase C-delta. Journal of Leukocyte Biology (2011). 90:235-247.
PCT/US2015/016447 International Search Report and Written Opinion dated May 14, 2015; 11 pages.
PCT/US2015/016447 International Preliminary Report on Patentability dated Aug. 23, 2016; 10 pages.
Jia Bei et al., Immunomodulatory Effect of Neutrophils in Bacterial Infection, World Notes on Antibiotics, 2004, vol. 25(2), pp. 61-63 cited in CN 201380041537.6 Office Action dated May 18, 2017, 24 pages.
EP 15751576.8 Extended Search Report dated Sep. 18, 2017, 11 pages.
Ding et al., Retinoid Agonist Am80-Enhanced Neutrophil Bactericidal Activity Arising from Granulopoiesis in vitro and in Neutropenic Mouse Model, Blood, 2013, vol. 121, pp. 996-1007.
Dunn et al., Lenograstim: An Update of its Pharmacological Properties and Use in Chemotherapy-Induced Neutropenia and Related Clinical Settings, Drugs, 2000, vol. 59, pp. 681-717.
Hematol, Acute Promyelocytic Leukemia and Differentiaion Therapy: Molecular Mechanisms of Differentiation, Retinoic Acid Resistance and Novel Treatments, APL and Differentiation Therapy, 2009, vol. 26, pp. 47-61.
Hubel et al., Current Status of Granulocyte (Neutrophil) Transfusion Therapy for Infectious Diseases, The Journal of Infectious Disease, 2001, vol. 183, pp. 321-328.
Tsurumi et al., The Combined Effects of All-Trans Retinoic Acid and Granulocyte Colony-Stimulating Factor as a Differentiation Induction Therapy for Acute Promyelocytic Leukemia, Internal Medicine, 1993, vol. 32(8), pp. 648-650.
Usuki et al., Administration of Granulocyte Colony-Stimulating Factor during Remission Induction Therapy with All-Trans Retinoic Acid for Acute Promyelocytic Leukemia, Internal Journal of Hematology, 1996, vol. 64, pp. 213-219.
Beekman et al., G-CSF and its Receptor in Myeloid Malignancy, 2010, Blood, vol. 115(25), pp. 5131-5136.
Gianni, AM580, A Stable Benzoic Derivative of Retinoic Acid, Has Powerful and Selective Cyto-Differentiating Effects on Acute Promyelocytic Leukemia Cells, 1996, Blood, vol. 87(4), pp. 1520-1531.
Masue Imaizumi, Molecular Mechanism of the Leukemogenesis and Differentiation-Induction in Acute Promyelocytic Leukemia, 2002, The Japanese Journal of Pediatric Hematology, vol. 16, pp. 50-61.
Montrone et al., Retinoids as Critical Modulators of Immune Functions: New Therapeutic Perspectives for Old Compounds, 2009, Endocrine, Metabolic & Immune Disorders, vol. 9(2), pp. 1-19.
Zhong, Novel Retinoic Acid Receptor Alpha Agonists for Treatment of Kidney Disease, 2011, PLoS One, vol. 6(11), e27945.

* cited by examiner

METHODS FOR TREATING NEUTROPENIA USING RETINOID AGONISTS

CROSS-REFERENCE TO RELATED APPLICATIONS

This application is the National Phase of International Application PCT/US2013/044828, filed Jun. 7, 2013, which designated the U.S. and that International Application was published under PCT Article 21(2) in English, which claims the benefit of the filing date of U.S. Provisional Application No. 61/656,815, filed Jun. 7, 2012, the disclosures of each of which are incorporated herein by reference in their entirety.

STATEMENT REGARDING FEDERALLY SPONSORED RESEARCH OR DEVELOPMENT

This invention was made with government support under Grant Nos. CA111440 and CA120512 awarded by the National Institutes of Health. The government has certain rights in the invention.

FIELD OF INVENTION

The invention is directed to methods for treating, inhibiting, reducing and/or promoting prophylaxis of neutropenia in subject in need thereof comprising administering a retinoid agonist, for example, tamibarotene.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Neutrophils, the most common granulocytes, constitute up to 70% of circulating leukocytes that primarily defend against pathogen infections. Cancer chemotherapy-induced neutropenia is a hematological disorder marked by large decreases in the number of neutrophils in the bloodstream. It has been more than two decades since G-CSF was first used to treat acquired and congenital neutropenia[1,2] by promoting granulopoiesis of HSC. Because of the low therapeutic index of G-CSF, its adverse effects of administration, and the risk of malignant transformation,[2] neutropenia induced by chemotherapy in oncology remains a major source of the morbidity, mortality, and healthcare expenses.[3,4] Recent studies show that in contrast to PBN, the impaired bacterial killing in neutrophils induced by G-CSF from CD34+ cells is associated with a lack of mature granules, due to abnormal granulopoiesis early in the differentiation process.[5] Thus, success in devising more effective therapy for neutropenia may depend on determining how granulopoiesis is coordinated with the development of neutrophil-based immunity.

The retinoid agonist Am80[6-8] is designed to ameliorate the side effects of all-trans retinoic acid (RA) through its selective binding to retinoic acid receptor alpha (RARα),[6,9,10] a transcription factor activated by RA[11,12] to regulate granulocytic differentiation of both leukemic myeloblasts and HSC.[13-17] RA, a naturally occurring form of vitamin A, plays key roles in the development of the body plan and induces the differentiation of many types of normal and malignant cells.[18-20] To date, RA treatment of acute promyelocytic leukemia (APL) represents the best example of successful differentiation-induction therapy in clinical oncology,[21] however, the side effects associated with RA therapy are generally serious and RA resistance is a common event.[22-24] Several studies have demonstrated that RARα regulates Am80-induced granulocytic differentiation.[25-27] Moreover, Am80 is approximately 10-fold more efficient, with lower toxicity, than either RA or other retinoids used as differentiation therapy in APL patients.[7,8,28] Currently, Am80 has been approved for the treatment of APL in Japan[7,8] and tested clinically for several other cancers/diseases in the US and Europe (http://www.cytrx.com/tami-barotene.html; http://clinicaltrials.gov). The advances in the use of Am80 to induce granulocytic differentiation led us to test this agent as a means to enhance neutrophil bactericidal activity arising from granulopoiesis during immune development. We report here that Am80 possesses significantly greater activity than G-CSF as an inducer of neutrophil differentiation and immune development, likely through its promotion of HSC-derived granulopoiesis by mediating the differential effects of CD66 on CD18 activation.

SUMMARY OF THE INVENTION

The invention provides methods for treating, inhibiting and/or reducing the severity of neutropenia, acute bacterial infection, cancer-chemotherapy induced neutropenia and/or various forms of congenital neutropenia in subjects in need thereof. The methods include providing a composition that includes a retinoid agonist and administering an effective amount of the composition to the subject so as to treat, inhibit and/or reduce the severity of neutropenia in the subject. The methods further comprise administering additional therapeutic agents concurrently or sequentially with the compositions of the invention so as to for treat, inhibit and/or reduce the severity of neutropenia, acute bacterial infection, cancer-chemotherapy induced neutropenia and/or various forms of congenital neutropenia in the subjects. In some embodiments, the retinoid agonist is any one or more of tamibarotene (AM80), CH55, ITYA (IT-YA-01115) or a combination thereof.

The invention also provides pharmaceutical compositions and kits for treating, inhibiting and/or reducing the severity of neutropenia, acute bacterial infection, cancer-chemotherapy induced neutropenia and/or various forms of congenital neutropenia in subjects in need thereof. The pharmaceutical compositions and kits include quantities of retinoid agonists. In some embodiments, the retinoid agonist is any one or more of tamibarotene (AM80), CH55, ITYA (IT-YA-01115) or a combination thereof.

BRIEF DESCRIPTION OF FIGURES

Exemplary embodiments are illustrated in the referenced figures. It is intended that the embodiments and figures disclosed herein are to be considered illustrative rather than restrictive.

(FIG. 8A) G-CSF induced a remarkably accelerated neutrophil recovery compared with mice treated with Am80 or vehicle at day 5. (FIG. 8B) Analysis of PB neutrophils at day 5. *G-CSF vs. Am80, $P<1.2\times10^{-6}$; G-CSF vs. control, $P<4.0\times10^{-5}$; G-CSF vs. vehicle, $P<8.2\times10^{-8}$; Am80 vs. vehicle, $P<1.3\times10^{-6}$; Am80 vs. control, $P<0.016$. (FIG. 8C) Phagocytotic and bactericidal activities of neutrophils, isolated from PB of different mice, were reflected by the number of extracellular bacteria, phagocytized bacteria, and killed bacteria after exposing of isolated neutrophils to *S. aureus* in vitro. *Extracellular: AINs vs. GINs, $P<0.043$; AINs vs. C-MPBNs, $P<1.1\times10^{-4}$; MPBNs vs. C-MPBNs, $P<3.7\times10^{-4}$; GINs vs. C-MPBNs, $P<0.049$. *Phagocytosis: AINs vs. GINs, $P<0.026$; AINs vs. C-MPBNs, $P<0.02$; MPBNs vs. GINs, $P<0.042$; MPBNs vs. C-MPBNs, $P<0.003$; GINs vs. C-MPBNs, $P<0.009$. *Killing: AINs vs. GINs, $P<0.026$; AINs vs. C-MPBNs, $P<0.005$; MPBNs vs. GINs, $P<0.015$; MPBNs vs. C-MPBNs, $P<0.003$; GINs vs. C-MPBNs, $P<0.009$. (FIG. 8D) Accelerated recoveries of WBC and neutrophil were ceased at day 7 after 96 hours of stimuli with G-CSF orAm80 or vehicle. (FIG. 8E) Analysis of PB neutrophils at day 9. *G-CSF vs. control, $P<0.005$; Am80 vs. control, $P<3.9\times10^{-4}$; Am80 vs. vehicle, $P<0.03$; Vehicle vs. control, $P<0.03$. (FIG. 8F) AINs possessed significantly higher phagocytotic and bactericidal activities than do GINs at day 9, as 48 hours after cessation of accelerated neutrophil recovery. *Extracellular: AINs vs. GINs, $P<0.02$; AINs vs. C-MPBNs, $P<0.007$; MPBNs vs. GINs, $P<0.04$; MPBNs vs. C-MPBNs, $P<0.02$. *Phagocytosis: AINs vs. C-MPBNs, $P<0.034$; MPBNs vs. C-MPBNs, $P<0.043$. *Killing: AINs vs. C-MPBNs, $P<0.034$; MPBNs vs. C-MPBNs, $P<0.043$. (FIG. 8G) In vivo data showing that in neutropenic mice, Am80 induces sufficient effective neutrophils that display greater bactericidal activity than those by G-CSF. Twenty C57BL6/J mice were randomly divided into 4 groups for the experiments. A single dose of intraperitoneal injection of cyclophosphamide (CPA) of 200 mg/kg was performed at day 0. Am80 or G-CSF or vehicle was administrated after 4 hr of CPA injection for consecutive 3 days. Mouse neutropenia was induced 48-60 hr after CPA injection. After 16 hr of intraperitoneal injection of $3\times10^7$ *S. aureus*, experiment was performed at day 3. Purified neutrophils, were analyzed for their bactericidal activities by determining the numbers of viable extracellular bacteria in peritoneal cavity (FIG. 8G-i) and PB (FIG. 8G-ii). The numbers of viable bacteria were counted from 3 ml of PBS-washed peritoneal fluid as well as with an estimated 1.5 ml of total blood plasma. P value of viable bacteria in peritoneal cavity: Am80 vs. G-CSF, $P<2.4\times10^{-8}$; control vs. G-CSF, $P<4.7\times10^{-9}$; vehicle vs. G-CSF, $P<8.3\times10^{-3}$; Am80 vs. vehicle, $P<3.1\times10^{-9}$; Am80 vs. control, $P<0.038$. *Total viable extracellular bacteria of FIG. 8G-iii: Am80 vs. G-CSF, $P<1.9\times10^{-6}$; control vs. G-CSF, $P<9.4\times10^{-9}$; vehicle vs. G-CSF, $P<6.5\times10^{-4}$; Am80 vs. vehicle, $P<6.8\times10^{-7}$; control vs. Am80, $P<3.8\times10^{-5}$. Fold changes in viable bacteria was showed in FIG. 8G-iv. Viable bacteria in control group was used as a standard of 1 fold.

DETAILED DESCRIPTION OF THE INVENTION

Figure 1:
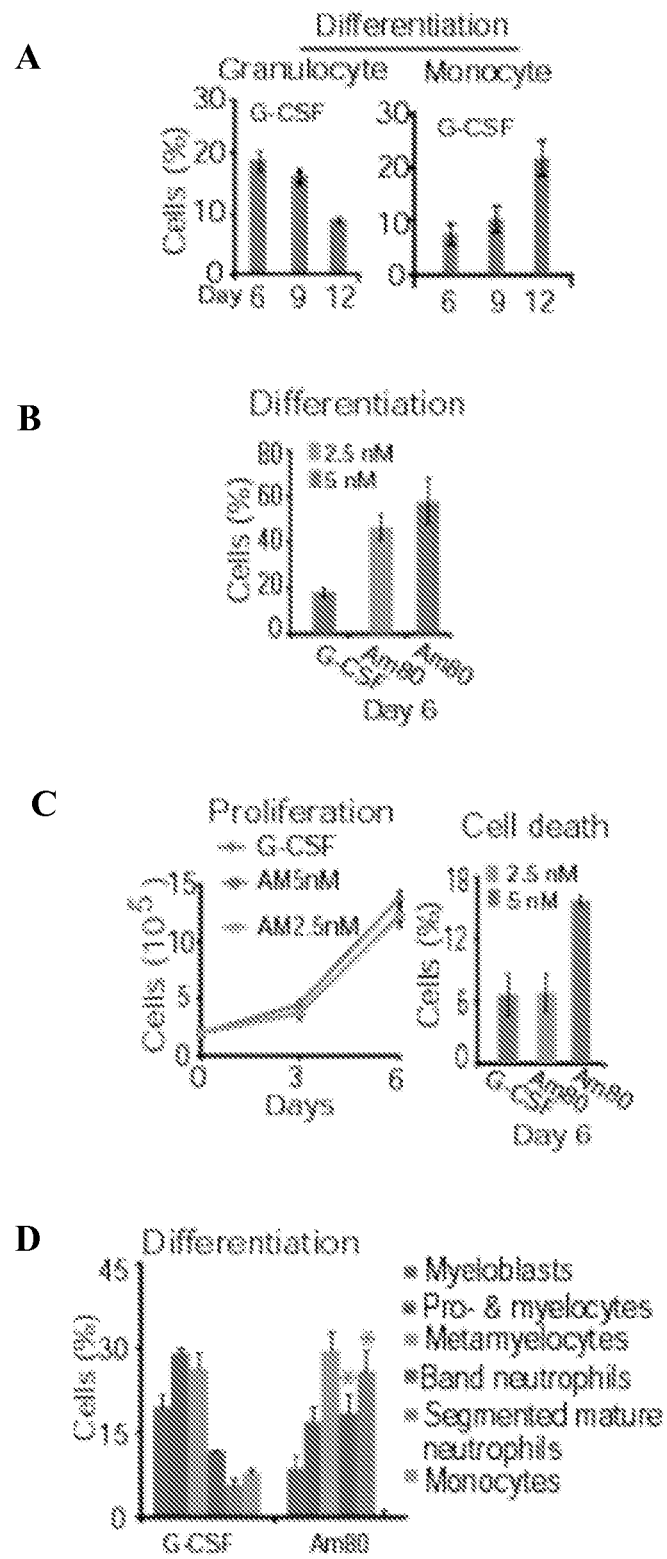
FIG. 1 depicts, in accordance with various embodiments of the present invention, that Am80 promotes neutrophil differentiation more effectively than G-CSF while showing similarly low toxicity. (A) Better granulocytic induction associated with lower monocytic induction in CD34+ cells treated with G-CSF for 6 vs. 9 or 12 days. (B & C) Reduced concentration of Am80 (2.5 nM) leads to more effective induction of granulocytic differentiation than achieved with G-CSF (panel B), while showing less cytotoxicity (panel C). (D) Overall comparison of Am80 and G-CSF under conditions found to be optimal for granulocytic differentiation.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Neutropenia" as used herein refers to abnormally low levels of neutrophils in the blood. Neutropenia may be due to decreased production of white blood cells (for example, due to, including but not limited to therapeutic agents that affect the bone marrow, hereditary/congenital disorders that affect the bone marrow, aplastic anemia, cancer, radiation therapy, Vitamin $B_{12}$, folate or copper deficiency and/or exposure to pesticides). Neutropenia may also be due to destruction of white blood cells (for example, due to, including but not limited to acute bacterial infections, certain autoimmune diseases, chemotherapy treatments and/or therapeutic agents). Neutropenia may also be due to sequestration and/or migration of white blood cells (for example, due to, including but not limited to, hemodialysis, malaria and/or bacterial infections). Certain medications such as flecainide, phenytoin, indomethacin, propylthiouracil, carbimazole, chlorpromazine, trimethoprim/sulfamethoxazole (cotrimoxazole), clozapine, ticlodipine may also result in neutropenia. The methods and compositions of the invention may be used to treat, inhibit, reduce the severity of and/or promote prophylaxis of neutropenia resulting from any of the above causes. The methods and compositions of the invention may also be used to treat, inhibit, reduce the severity of and/or promote prophylaxis of disease-states that result from any of the above causes of neutropenia by treating, inhibiting, reducing the symptoms of and/or promoting prophylaxis of neutropenia.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Therapeutically effective amount" as used herein refers to that amount which is capable of achieving beneficial results in a mammalian subject with neutropenia. A therapeutically effective amount can be determined on an individual basis and will be based, at least in part, on consideration of the physiological characteristics of the mammal, the type of delivery system or therapeutic technique used and the time of administration relative to the progression of the disease.

Despite advances in the therapeutic use of recombinant granulocyte colony-stimulating factor (G-CSF) to promote granulopoiesis of human hematopoietic stem cells (HSC), neutropenia remains one of the most serious complications of cancer chemotherapy. Using an ex vivo model to induce granulocytic differentiation of primitive CD34+ hematopoietic cells, we discovered that Am80 (tamibarotene), a novel retinoid agonist, is more potent than G-CSF in coordinating neutrophil differentiation and immunity development. Functional analysis and in situ imaging of granule production, *E. coli* infection, and bacterial killing demonstrated that similar to human peripheral blood neutrophils (PBN), Am80-induced neutrophils (AIN) possessed greater bactericidal activities than G-CSF-induced neutrophils (GIN). In contrast to GIN but similar to PBN, the enhanced bacterial killing by AIN was associated with greater co-expression of CD66 antigen with the integrin $\beta 2$ subunit CD18. Consistently, anti-CD18 antibody neutralized Am80-induced bactericidal activities of AIN. Thus, AIN appears to offer a more effective means of promoting neutrophil differentiation and bactericidal activities compared to G-CSF, likely through coordinating the functional interaction of CD66 with CD18 to enhance the development of neutrophil immunity during granulopoiesis. These findings herein provide a molecular rationale for devising novel treatment against neutropenia by using Am80 as a cost-effective treatment option.

Accordingly, the invention provides methods for treating neutropenia in a mammalian subject in need thereof. The method comprises providing a composition comprising a retinoid agonist and administering a therapeutically effective amount of the composition to the subject so as to treat neutropenia in the subject. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof The invention further provides methods for reducing the severity of neutropenia in a mammalian subject in need thereof. The method comprises providing a composition comprising a retinoid agonist and administering a therapeutically effective amount of the composition to the subject so as to reduce the severity of neutropenia in the subject. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

The invention also provides methods for inhibiting neutropenia in a mammalian subject in need thereof. The method comprises providing a composition comprising a retinoid agonist and administering a therapeutically effective amount of the composition to the subject so as to inhibit neutropenia in the subject. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

Additionally, the invention provides methods for promoting prophylaxis of neutropenia in a subject in need thereof. The method comprises providing a composition comprising a retinoid agonist and administering a therapeutically effective amount of the composition to the subject so as to promote prophylaxis of neutropenia in the subject. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

The invention further provides a method for treating, inhibiting and/or reducing the severity of cancer-chemotherapy induced neutropenia in a subject in need thereof. The method comprises providing a composition comprising a retinoid agonist and administering a therapeutically effective amount of the composition to the subject to treat, inhibit and/or reduce the severity of cancer-chemotherapy induced neutropenia. The method further comprises administering a chemotherapeutic agent. In one embodiment, the chemotherapeutic agent and the composition comprising a retinoid agonist are administered concurrently. In another embodiment, the chemotherapeutic agent and the composition comprising a retinoid agonist are administered sequentially. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

Examples of chemotherapeutic agents include but are not limited to Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof The invention also provides a method for treating, inhibiting, reducing the severity of and/or promoting prophylaxis of an acute bacterial infection in a subject in need thereof. The method comprises providing a composition comprising a retinoid agonist, providing a composition comprising an anti-bacterial therapeutic agent and administering a therapeutically effective amount of each of the compositions to the subject to treat, inhibit, reduce the severity of and/or promote prophylaxis of acute bacterial infection in the subject. In one embodiment, the composition comprising the retinoid agonist and the composition comprising the anti-bacterial therapeutic agent are administered concurrently. In another embodiment, the composition comprising the retinoid agonist and the composition comprising the anti-bacterial therapeutic agent are administered sequentially. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

The invention further provides methods for treating, inhibiting, reducing the severity of and/or promoting prophylaxis of congenital neutropenia (including but not limited to Kostmann syndrome, cyclic neutropenia or Chediak Higashi) in a mammalian subject in need thereof. The method comprises providing a composition comprising a retinoid agonist and administering a therapeutically effective amount of the composition to the subject so as to treat, inhibit, reduce the severity of and/or promote prophylaxis of congenital neutropenia in the subject. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

In some embodiments, the mammalian subjects in need of the compositions described herein are patients with decreased white blood cell production resulting from, including but not limited to, medication that affects the bone marrow (such as cancer drugs, antipsychotic drugs, anticonvulsant drugs), hereditary and/or congenital disorders that affect the bone marrow, patients undergoing radiation therapy, vitamin $B_{12}$ deficiency, folic acid deficiency or a combination thereof.

In further embodiments, the mammalian subjects in need of the compositions described herein are subjects with damaged, destroyed and/or reduced amounts of white blood cells due to, including but not limited to, acute bacterial infections, autoimmune disorders (such as systemic lupus erythematosus), use of sulfonamide medications, or a combination thereof.

In additional embodiments, the mammalian subjects in need of the compositions described herein are subjects undergoing sequestration and/or migration of white blood cells (such as neutrophils) due to, including but not limited to, hemodialysis, malaria, bacterial infections or a combination thereof.

In various embodiments, the composition of the invention comprising a retinoid agonist may be administered concurrently or sequentially with other therapeutic agents including but not limited to chemotherapeutic agents and/or radiation therapy. Chemotherapeutic agents and/or radiation therapy often reduce the number of white blood cells, resulting in neutropenia. Administering the composition of the invention concurrently or sequentially with the chemotherapeutic agents and/or radiation therapy may inhibit and/or reduce the severity of neutropenia. In various embodiments, the composition of the invention comprising a retinoid agonist is administered before, during or after administration of chemotherapeutic agents and/or radiation therapy. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

Similarly, the composition comprising a retinoid agonist may be administered concurrently or sequentially with anti-convulsant and/or antipsychotic drugs so as to inhibit and/or reduce the severity of neutropenia resulting from the use of said drugs. In various embodiments, the composition of the invention comprising a retinoid agonist is administered before, during or after administration of anticonvulsant and/or antipsychotic drugs. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

Additionally, the composition comprising a retinoid agonist may be administered concurrently or sequentially with therapeutic agents used to treat acute bacterial infections, fungal infections and/or autoimmune diseases so as to inhibit and/or reduce the severity of neutropenia that may occur due to bacterial and fungal infections and/or autoimmune diseases and/or due to the therapeutic agents that may be used to treat bacterial infection, fungal infection and/or autoimmune diseases. In various embodiments, the composition of the invention comprising a retinoid agonist is administered before, during or after administration of therapeutic agents used to treat acute bacterial infections, fungal infections and/or autoimmune diseases. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof.

In various embodiments, the retinoid agonist is administered intravenously, intramuscularly, intraperitonealy, orally or via inhalation. In one embodiment, the retinoid agonist is tamibarotene.

In various embodiments, the effective amount of the retinoid agonist is any one or more of about 0.01 to 0.05 μg/kg/day, 0.05-0.1 μg/kg/day, 0.1 to 0.5 μg/kg/day, 0.5 to 5 μg/kg/day, 5 to 10 μg/kg/day, 10 to 20 μg/kg/day, 20 to 50 μg/kg/day, 50 to 100 μg/kg/day, 100 to 150 μg/kg/day, 150 to 200 μg/kg/day, 200 to 250 μg/kg/day, 250 to 300 μg/kg/day, 300 to 350 μg/kg/day, 350 to 400 μg/kg/day, 400 to 500 μg/kg/day, 500 to 600 μg/kg/day, 600 to 700 μg/kg/day, 700 to 800 μg/kg/day, 800 to 900 μg/kg/day, 900 to 1000 μg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. In some embodiments, the retinoid agonist is any one or more of tamibarotene (AM80), CH55, ITYA (IT-YA-01115) or a combination thereof. In an embodiment the retinoid agonist is tamibarotene (AM80), an analog and/or a salt thereof. Typical dosages of an effective amount of a retinoid agonist, can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the compositions of the invention comprising the retinoid agonist may be administered once a day (SID/QD), twice a day (BID), three times a day (TID), four times a day (QID), or more, so as to administer an effective amount of the retinoid agonist to the subject, where the effective amount is any one or more of the doses described herein.

The invention also provides methods for identifying retinoid agonist. The method includes contacting CD34+ cells with a molecule of interest, further contacting CD34+ cells and the molecule of interest with an antigen to stimulate an immune response and assessing whether the contact between CD34+ cells, the molecule of interest and the antigen results in increased secretion of lactoferrin, LL-37 or a combination thereof. In an embodiment, increased secretion of lactoferrin, LL-37 or a combination thereof is indicative that the molecule of interest is a retinoid agonist.

Assays that may be employed to identify compounds that are retinoid agonists include but are not limited to microarray assay, quantitative PCR, Northern blot assay, Southern blot assay, Western blot assay immunohistochemical assays, binding assays, gel retardation assays or assays using yeast two-hybrid systems. A person skilled in the art can readily employ numerous techniques known in the art to determine whether a particular agent/molecule of interest is a retinoid agonist.

In various embodiments, the subject is selected from the group consisting of human, non-human primate, monkey, ape, dog, cat, cow, horse, rabbit, mouse and rat.

Pharmaceutical Compositions

In various embodiments, the present invention provides pharmaceutical compositions including a pharmaceutically acceptable excipient along with a therapeutically effective amount of a retinoid agonist, such as tamibarotene (AM80), CH55, ITYA (IT-YA-01115) or a combination thereof. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Kits of the Invention

The invention also provides a kit for the treatment of neutropenia, inhibition of neutropenia, reduction of neutropenia or promotion of neutropenia prophylaxis in a subject in need thereof. The kit comprises a composition comprising a retinoid agonist and instructions for use of the composition for treating, inhibiting and/or reducing the severity of neutropenia, acute bacterial infection, cancer-chemotherapy induced neutropenia and/or various forms of congenital neutropenia in subjects in need thereof. In some embodiments, the retinoid agonist is any one or more of tamibarotene (AM80), CH55, ITYA (IT-YA-01115) or a combination thereof. In one embodiment, the retinoid agonist is tamibarotene (AM80).

The kit is an assemblage of materials or components, including at least one of the inventive compositions. Thus, in some embodiments the kit contains a composition including a retinoid agonist, such as any one or more of tamibarotene (AM80), CH55, ITYA (IT-YA-01115) or a combination thereof, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, reduce the severity of, inhibit or prevent neutropenia in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing a a retinoid agonist, such as any one or more of tamibarotene (AM80), CH55, ITYA (IT-YA-01115) or a combination thereof. The packaging material generally has an external label which indicates the contents and/or purpose of the kit and/or its components.

EXAMPLES

Example 1

Cells and Cell Culture

Normal human primitive umbilical cord blood CD34+ cells were from AllCells (Emeryville, Calif.). CD34+ cells were expanded[29] about 50× by using StemSpan serum-free medium (StemCell Technologies, Vancouver, Canada) for 6 days according to the manufacturer's protocol. To induce granulopoiesis, CD34+ cells were cultured with myeloid medium supplemented with 25 ng/ml of G-CSF[17,29] for 6-12 days. Lymphoid and erythroid cells were blocked during granulopoiesis by addition of hydrocortisone and exclusion of erythropoietin.[17,29] All-trans retinoic acid (RA) was from Sigma (St. Louis, Mo.), while the retinoid agonists Am80, CH55, and IT-YA-01115 (ITYA) were from Research Foundation ITSUU Laboratory (Tokyo, Japan). Each retinoid compound was dissolved in ethanol. The experimentally determined conditions, using 25 ng/ml of G-CSF[17,29] or 2.5 nM of Am80 for granulocytic induction of 6 days (FIG. 1), were applied in the studies.

Human PBN

Peripheral venous blood was taken from healthy volunteers in accord with a protocol approved by the Children's Hospital Los Angeles/University of Southern California Keck School of Medicine (CHLA/USC) Committee on Clinical Investigations. Each 20 ml of blood was drawn into Vacutainer Coagulation Tubes (BD Biosciences, San Jose, Calif.) and diluted with 1 volume of HBSS at room temperature. The diluted blood was loaded onto 10 mL of Ficoll-paque premium (GE Healthcare, Piscataway, N.J.) and centrifuged at 400×g for 40 min. The collected PBN-erythrocyte layer was then mixed with 15 mL of 3% dextran T500 (Sigma) for sedimentation for 2 hr at room temperature. The erythrocytes were removed by hypotonic lysis with sterile water for 18 sec, and the PBN-rich layer was then collected with centrifugation. The purity of collected PBN was >95%, as measured by morphological analysis with Wright-Giemsa stain. Freshly purified PBN were used in the assays immediately after completion of PBN isolation.

Cell Proliferation and Cell Death

Cell proliferation was determined by cell count with a standard hemocytometer, as described.[17,29] Briefly, equal numbers of cells plated in triplicate were counted for up to 13 days after 72 hr of plating. By using trypan blue exclusion, cell proliferation and its associated cell death in the cultures were measured simultaneously.

Morphologic Analysis of Granulocytic Differentiation

Cell suspensions were cytocentrifuged onto Micro slides, followed by methanol fixation and stained with Wright-Giemsa (Sigma) as described.[17,29] The morphologic indicators of differentiation were evaluated under a Zeiss Axioplan microscope, and images were color balanced with Adobe Photoshop as described.[17]

Transmission Electron Microscopy

Ultrastructural study of neutrophils and bacterial infection was performed by members of Electron Microscopy Laboratory, Department of Pathology and Laboratory Medicine, CHLA/USC. The procedures are detailed below.

Western Blotting

Western blotting (WB) was performed as described.[15] Antibodies for lactoferrin (Abcam, Cambridge, UK), MMP-9 (Merck Chemicals, Darmstadt, Germany), and LL-37 (Biolegend, San Diego, Calif.) were used in analyses.

Degranulation Analysis

Cells were incubated with or without *E. coli* DH5α (MOI of 5; cell to bacteria ratio 1:5) in serum-free DMEM medium for 30 min at 37° C. Both cell pellets and supernatants were collected by 3,000-rpm centrifugation for 7 min. The cell pellets were suspended with 100 μg/ml of gentamicin and incubated at 37° C. for 1 hr, followed by collection of cells and extraction of cellular proteins. The supernatant was filtered with a 0.22-μm filter (Pall corporation, Ann Arbor, Mich.) and proteins in the supernatant were then concentrated by using an Amicon Ultra-4 centrifugal filter unit designed to collect proteins with a mass greater than 3,000 daltons (Millipore, Billerica, Mass.). The quantity of the proteins was measured by using Bio-Rad DC Protein Assay (Hercules, Calif.).[29] The change in granule protein levels with or without *E. coli* stimuli was analyzed in parallel by WB.

Phagocytosis and Bacterial Killing Assays

Each $5 \times 10^5$ to $2 \times 10^6$ of freshly purified PBN as well as ex vivo-induced GIN and AIN were suspended with 500 μl of culture medium (DMEM with 10% of FBS) in 1.5-ml tubes. Cells were incubated with log-phase *Escherichia coli* (*E. coli*) DH5α (provided by collaborator) or *Staphylococcus aureus* (*S. aureus*; ATCC) at an MOI of 5 or 10 at 37° C. for 15, 30, and/or 60 min, whereas bacteria in the absence of cells were used to determine growth. The samples with or without cells were centrifuged at 1000-rpm at each time point. Extracellular bacteria in the presence of cells were collected from the supernatants, and enumerated by plating different dilutions (20 μL each) on blood agar. Cell pellets collected from the samples infected with bacteria were further incubated with 100 μg/ml of gentamicin (Sigma) for 1 hr at 37° C. to kill external bacteria. Cells were then washed twice and lysed with 100 μL of 0.5% Triton X-100. Different-dilution aliquots (20 μL for each) of viable intracellular bacteria recovered from the cell lysates were plated on blood agar. The numbers of extracellular and viable intracellular bacteria at each time point were determined by CFU counts as described,[5,30] while the number of phagocytosed and killed bacteria was based on the counts of extracellular and viable intracellular bacteria to the number of relevant bacteria control in the neutrophil-free condition.[5,30]

Magnetic Sorting of CD15+ Neutrophils

Cells suspended in PBS containing 0.5% BSA and 2 mM EDTA were mixed with anti-CD15 antibodies conjugated to magnetic microbeads (Miltenyi Biotec, Bergish Gladbach, Germany) for incubation of 30 min at 4° C. CD15+ subpopulation was then purified by using magnetic sorter (Miltenyi Biotec, Bergish Gladbach, Germany) according to the manufacturer's protocol.

Statistical Analysis

Descriptive statistics, including means, standard deviations, and ranges, were computed when necessary and analyzed with Student's unpaired two-tailed t-test. P values of 0.05 or less were considered statistically significant.

In Situ Bactericidal Killing

Cells were incubated with *E. coli* or *S. aureus* for 15 min and/or 60 min, followed by collecting cells by 1,000-rpm centrifugation for 5 min. The cell pellets were suspended with 100 μg/mL of gentamicin and incubated at 37° C. for 1 hr. After washing of three times, cells were permeabilized with Cytofix/Cytoperm solution (BD Biosciences) at 4° C. for 20 min. The cells were washed again and re-suspended in PBS for labeling intracellular living and dead bacteria, using LIVE/DEAD BacLight Viability Kit (Life Technologies, Grand Island, N.Y.) according to manufacturer's protocol. Cells were spun onto micro-slides and examined under confocal microscope with 488- and 564-nm lines of krypton/argon laser. Fluorescent dye SYTO9-stained living bacteria with intact membranes appeared green, whereas dead bacteria with damaged membranes were stained in red with fluorescent dye propidium iodide (PI).

Immunofluorescence Detection of Bacterial Infection

GIN, AIN, and PBN were incubated with *E. coli* or *S. aureus* at MOI of 10 at 37° C. for 15 min and 60 min. Cells were fixed with 2% paraformaldehyde at room temperature for 20 min, followed by blocking with PBS containing 5% normal goat serum for 30 min. To block OmpA antigens of the bacteria retained on the cell surface after infection, cells were first incubated with anti-OmpA antibody for 1 hr at room temperature, followed by incubation with HRP-conjugated anti-rabbit IgG antibody at room temperature for 30 min in order to block the external primary antibody sites. After thoroughly washing, cells were permeabilized with permeabilization solution (BD Biosciences) for 20 min and then incubated with anti-OmpA antibody for labeling intracellular bacteria at room temperature for 1 hr. Following incubation of cells with goat anti-rabbit IgG antibody conjugated to FITC for 30 min, cells were then spun onto Micro slides and mounted with vectashield anti-fade solution (Vector laboratories, Burlingame, Calif.). The FITC-stained bacteria were imaged with confocal microscope.

Flow Cytometric Analysis

Anti-human CD66-PE (recognizing CD66a, CD66c, CD66d, and CD66e subunits), CD11b-APC, CD18-FITC, and CD66b-PE antibodies as well as their corresponding isotypes were from BD Biosciences. Anti-human CD66a-PE and its corresponding isotype were from R&D systems (Minneapolis, Minn.). Data were acquired and analyzed with FlowJo software (version 7.6.5; Tree star, Ashland, Oreg.).

Example 2

Am80 Promotes Neutrophil Differentiation more Effectively than does G-CSF

Figure 5:
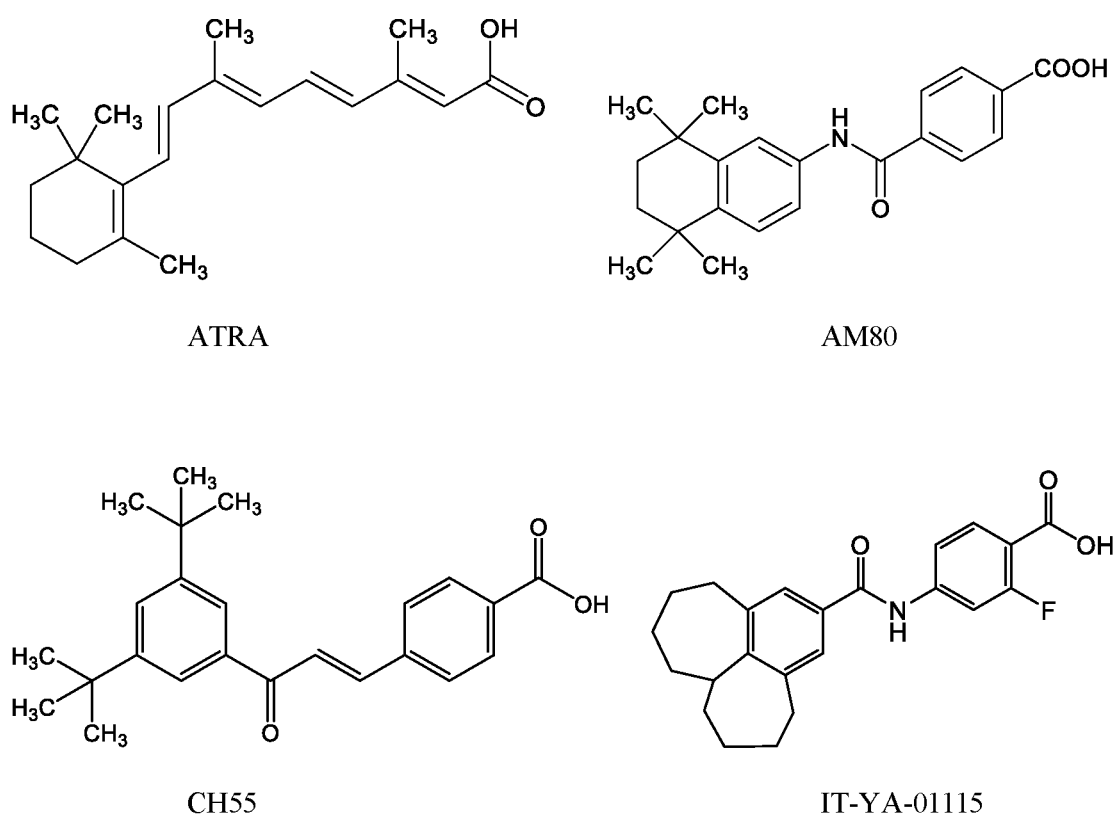
FIG. 5 depicts, in accordance with various embodiments of the present invention, the structures of ATRA (RA) and newly synthetic retinoid agonists Am80, CH55, and IT-YA01115 (IT-YA).
Figure 6:
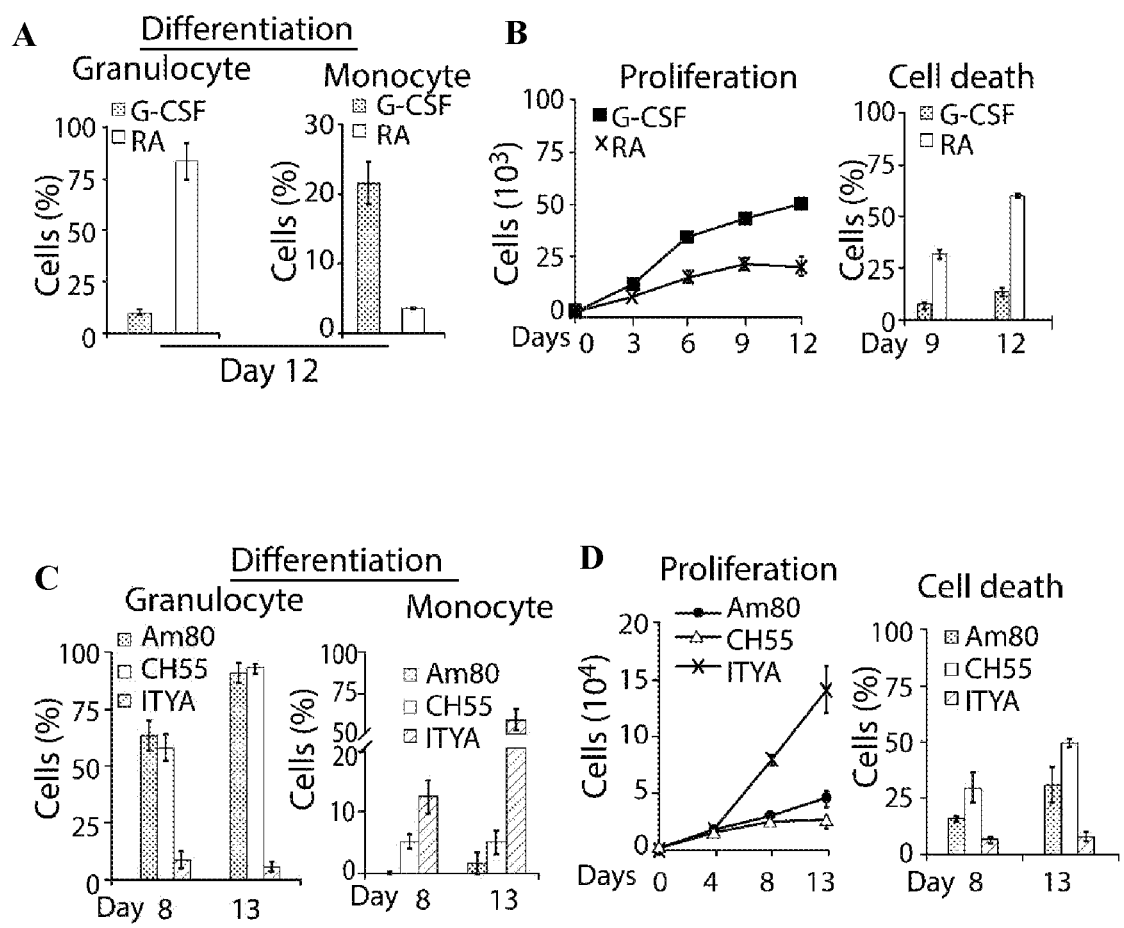
FIG. 6 depicts, in accordance with various embodiments of the present invention, that Am80 induces granulocytic morphologic differentiation of CD34+ cells more effectively than G-CSF and other retinoid compounds. (A-B) The higher efficiency of RA on inducing granulocytic differentiation than G-CSF (panel A) was associated with significant cell death (panel B). Lower efficiency in inducing differentiation of CD34+ cells to granulocytes by G-CSF was associated with higher monocytic induction on day 12 (panels A). (C-D) Am80 (10 nM) possessed similar efficiency on inducing granulocytic differentiation compared to RA and CH55 (panels A, C), while showing less monoytic induction than G-CSF or IT-YA or CH55 (panels A, C) and lower rate of cell death than RA and CH55 (panels B, D).

Am80, CH55, and ITYA are a group of retinoid agonists that were synthesized by introducing heteroatoms into RA-like structures (FIG. 5). Because all these agonists possess potent retinoidal activities, the efficiencies of these compounds were compared with G-CSF and RA in inducing granulopoesis from CD34+ cells, using our established methodology.[17,29] The inventors demonstrated that G-CSF was less effective than RA at inducing morphologic differentiation of CD34+ cells to granulocytes, accompanied by a higher induction of monocytes (FIG. 6A). However, G-CSF induced greater cell proliferation and a lower rate of cell death compared to RA (FIG. 6B). Of the other retinoid agonists, Am80 (10 nM) and CH55 (5 nM) promoted >75% granulocytic differentiation by day 13, in contrast to ITYA (5 nM) that produced >60% monocytes (FIG. 6C). Although both Am80 and CH55 inhibited cell proliferation (FIG. 6D) as did RA (FIG. 6B), the cell death rate associated with Am80 treatment was lower than seen with either CH55 or RA (FIG. 6B, 6D). Together, these data show that G-CSF is significantly less efficacious as an inducer of granulocytic differentiation than are RA, CH55, and Am80, whereas ITYA mainly induces monocytic differentiation. While Am80, RA, and CH55 promote granulocytic differentiation with similar effectiveness, Am80 induces a lower rate of cell death.

Because the lower level of CD34+ cell differentiation to granulocytes induced by G-CSF on day 12 was associated with a higher level of monocytic induction, G-CSF may induce granulocytic differentiation more effectively in a short period of time. Thus, CD34+ cells were treated with G-CSF for 6, 9, and 12 days. By analysis of morphologic differentiation of those cells, the inventors found more effective granulocytic differentiation with the lowest rate of monocytic induction on day 6 compared to either day 9 or day 12 (FIG. 1A). Using this optimal 6-day induction condition, G-CSF and Am80 were compared for their ability to induce granulocytic differentiation of CD34+ cells. Because 10 nM of Am80 induced more cell death (FIG. 6C), a reduced Am80 concentration (2.5 nM or 5 nM) was substituted in the tests. The results showed that 2.5 nM of Am80 not only profoundly induced granulocytic differentiation with negligible monocytic induction (FIG. 1B), but also produced less toxicity than 5 nM of Am80 (FIG. 1C). Hence, these results indicate that the 6-day optimal induction period for G-CSF is also suitable for Am80 (2.5 nM), prompting us to apply such drug exposure time and drug dose for the remainder of the study.

Neutrophil differentiation of CD34+ cells was analyzed on the promyelocyte, myelocyte, metamyelocyte, and band neutrophil stages to segmented mature neutrophil stage. CD34+ cells were treated with G-CSF or Am80 for 6 days. Granulocytic morphologic analysis showed that sequential development of neutrophils was sufficiently induced by Am80. By contrast, G-CSF induced more myeloblasts as well as promyelocytes and myelocytes than banded and segmented neutrophils (FIG. 1D). In addition, G-CSF consistently induced monocytes (about 10%; FIG. 1A, 1D). These results demonstrate that Am80 is more effective than G-CSF in inducing neutrophil morphologic differentiation, with a similar rate of cellular toxicity.

AIN are more Effective than GIN in Producing and Secreting Granules

During neutrophil differentiation, heterogeneous populations of granule proteins are produced sequentially and stored in cytoplasm for first-line defense against different pathogens.[32,33] The inventors investigated whether Am80-enhanced neutrophil maturation is associated with increased granule production. Neutrophils induced for 6 days from CD34+ cells by G-CSF and Am80 were analyzed by transmission electron microscopy. The ultrastructural images showed that, at the segmented neutrophil level, GIN possessed variable number of vesicles often containing less dense and amorphous material, together with few primary- and secondary-like granules. By contrast, vesicles found in AIN were frequently filled with dense material or with both amorphous and dense material. Compared to GIN, AIN contained increased numbers of primary- and secondary-like granules, as observed in PBN. Thus, the data indicate marked differences in vesicle formation and granule production between GIN and AIN.

The inventors verified whether Am80-induced granulocytic differentiation was indeed associated with sufficient granule production, and tested the degranulation ability of AIN upon bacterial stimuli. CD34+ cells were treated with G-CSF or Am80 for 6 days. The resultant GIN and AIN were than incubated with or without E. coli for 30 min, followed by protein extraction from both cell lysates and supernatants. WB analyses of granule production and secretion showed that lactoferrin, a secondary granule that has potent broad-spectrum anti-microbial activity,[34,35] was stored in AIN and secreted into the medium in sufficient quantities upon bacterial stimuli. By contrast, although the level of lactoferrin was increased with bacterial stimuli in GIN, the efficiency of lactoferrin secretion by GIN was much lower than seen with AIN (FIG. 2A). Similarly, a high level of secondary granule LL-37 was observed in AIN, and upon bacterial stimuli, LL-37 granules were effectively released into the medium. GIN, on the other hand, showed both lack of LL-37 production and degranulation (FIG. 2B). Thus, both lactoferrin and LL-37 are effectively produced and secreted by AIN but not GIN.

Even in the absence of E. coli, GIN secreted MMP-9 (tertiary granules) into the medium, and that this secretion was inhibited by bacterial stimuli (FIG. 2C). On the other hand, although E. coli enhanced MMP-9 expression in AIN, bacterial stimuli failed to induce AIN to secrete MMP-9 (FIG. 2C). These observations indicate possible defects in MMP-9 induction or degranulation (or both) in ex vivo-induced GIN and AIN.

Figure 2:
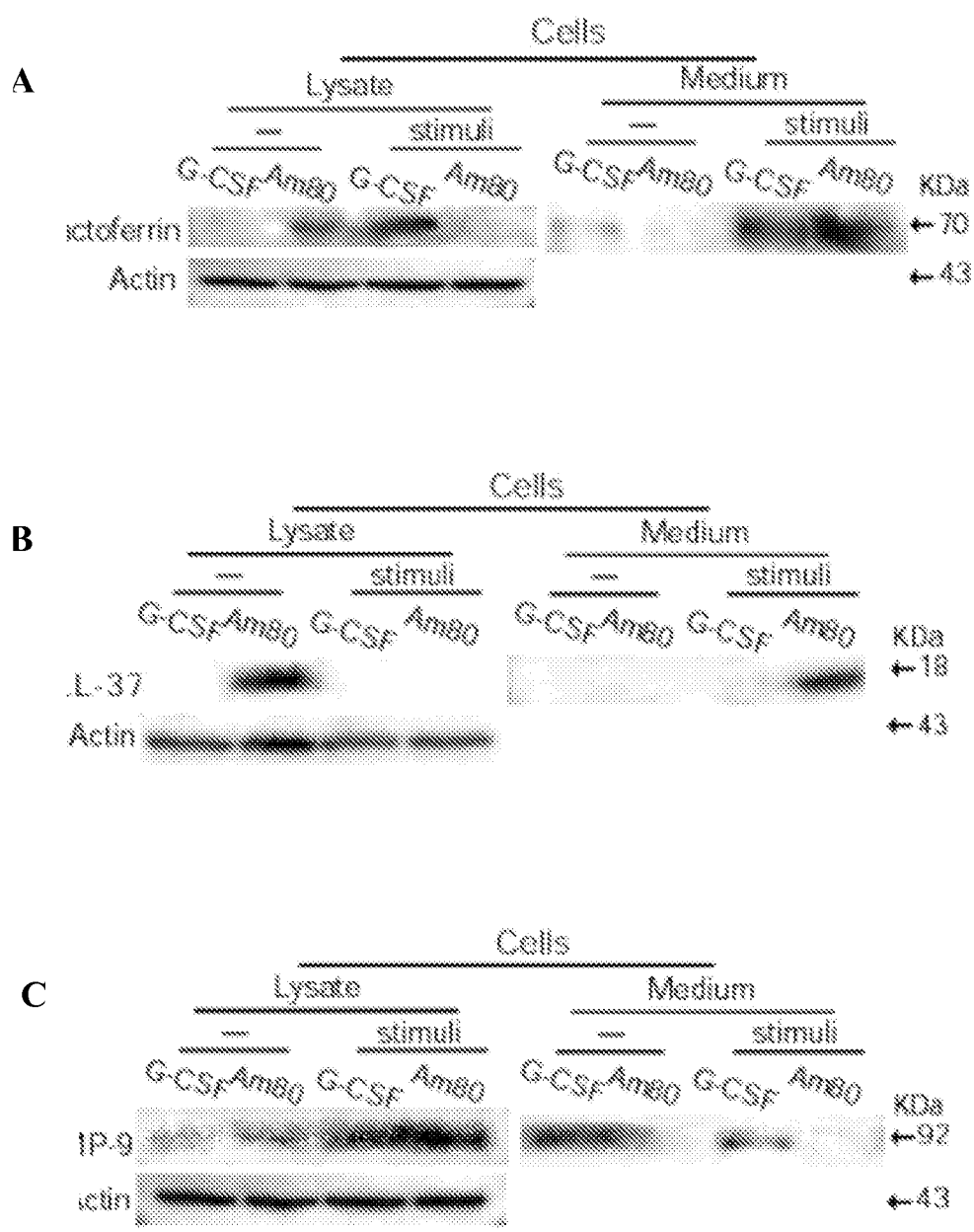
FIG. 2 depicts, in accordance with various embodiments of the present invention, that Am80-induced neutrophils (AIN) produce and secrete granules more effectively than do G-CSF-induced neutrophils (GIN). (A) Effective secretion of lactoferrin by AIN vs. GIN upon *E. coli* stimuli. (B) Greater production and degranulation of LL-37 by AIN vs. GIN. (C) Increased abundance of intracellular MMP9 upon *E. coli* stimuli but insufficient degranulation in both GIN and AIN.
Figure 3:
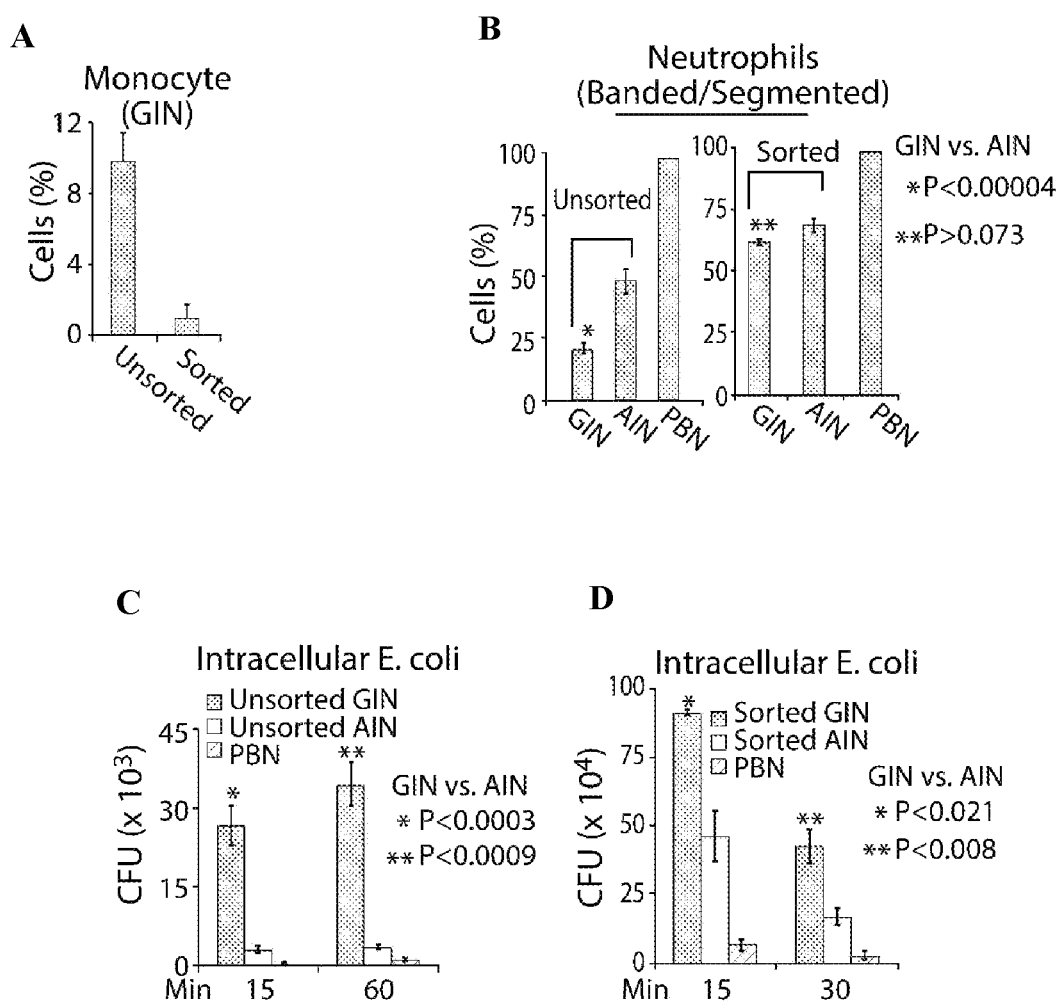
FIG. 3 depicts, in accordance with various embodiments of the present invention, that both unsorted and sorted AIN with anti-CD15 antibody display a higher capacity for clearance of bacteria than do unsorted and sorted GIN. (A) shows the quantification of monocytes (GIN). (B) shows the quantification of band/segmented neutrophils GIN vs. AIN. (C & D) Comparison of the effect of unsorted and sorted GIN and AIN on the clearance of intracellular bacteria. Clearance efficiency was determined from the numbers of viable bacteria recovered from the intracellular compartment after infection.

AIN Possess Significantly Higher Phagocytic and Bactericidal Activities than do GIN The above studies show that Am80 is more effective than G-CSF in promoting both granulocytic morphologic differentiation and granule production/secretion (FIGS. 1, 2). The inventors determined whether this higher degree of neutrophil differentiation induced by Am80 translates into greater neutrophil immunity against bacterial infection. Because Am80 induces more band-form and segmented neutrophils than does G-CSF (FIG. 1), whether sorted band and segmented neutrophils from GIN and AIN possessed similar bactericidal activities was tested. Since neutrophils are CD15+ cells,[36] GIN and AIN were purified using anti-CD15 antibody conjugated to magnetic MicroBeads. After purification, the proportion of band/segmented neutrophils in unsorted GIN had increased from 21% to 63% in sorted GIN, similar to findings in sorted AIN (FIG. 3B). Moreover, the fraction of residual monocytes in sorted GIN was only about 1% (FIG. 3A). These unsorted and sorted GIN and AIN were then tested for their capacity to kill log-phase *E. coli*, together with freshly isolated/purified PBN consisting of >95% segmented neutrophils (FIG. 3B). Of note, the CFU counts indicated that only a few viable bacteria were recovered from intracellular compartments of PBN and unsorted AIN compared to unsorted GIN (FIG. 3C). As with the unsorted GIN, the sorted GIN were also significantly less able than sorted AIN to kill bacteria (FIG. 3D). The enhanced bacterial clearance in AIN was confirmed by in situ labeling of *E. coli*, using anti-OmpA antibody that specifically recognizes the outer membrane of *E. coli*. These results indicate that the levels of neutrophil differentiation arising from granulopoiesis induced by Am80 are essential to effective neutrophil immunity against bacterial infection. This observation is supported by the data that GIN with segmented neutrophil morphology still display a lower level of granule-like molecules and contain a greater number of less dense, amorphous vesicles.

Figure 4:
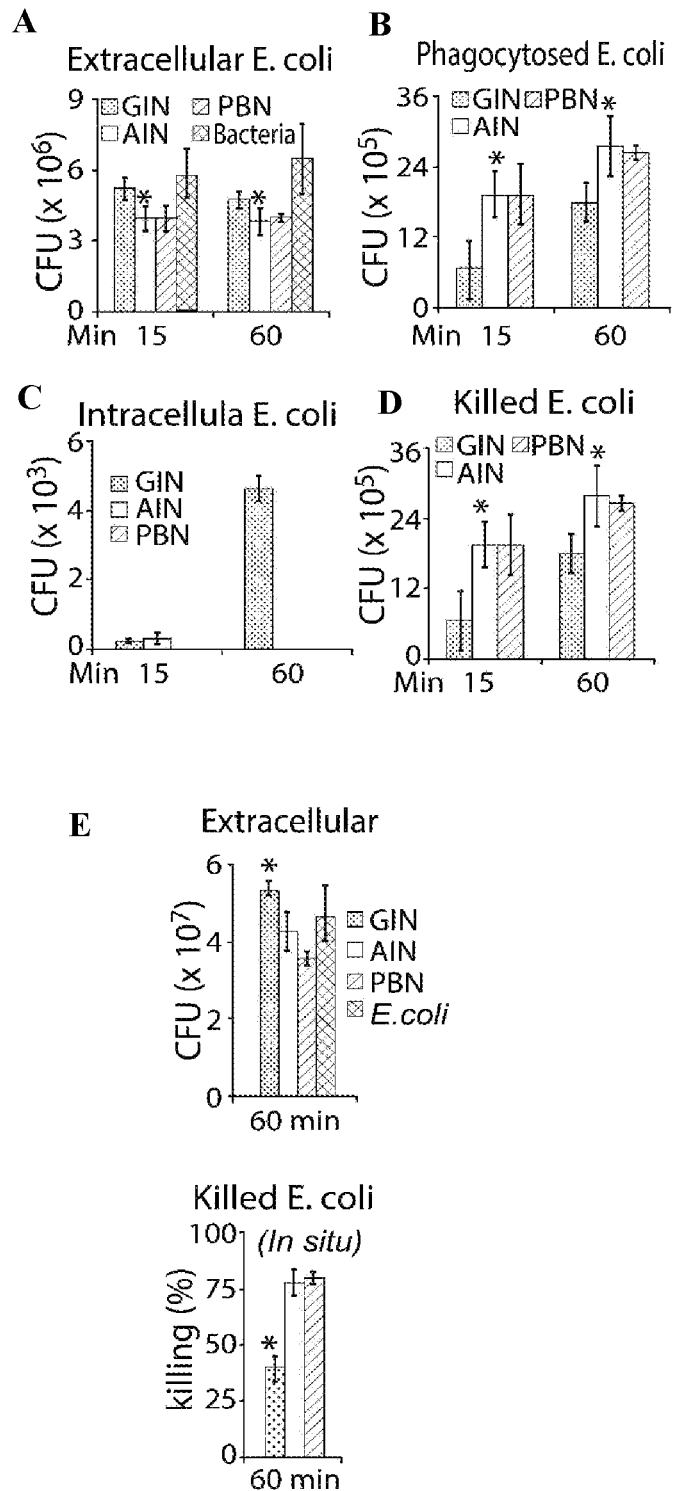
FIG. 4 depicts, in accordance with various embodiments of the present invention, that AIN possess significantly higher phagocytic and bactericidal activities than do GIN. (A-D) Phagocytic and bactericidal activities as determined by the number of extracellular bacteria (panel A), phagocytosed bacteria (panel B), recovered intracellular bacteria (panel C), and killed bacteria (panel D). There was a 1.26±0.01-fold increase in bacterial numbers over the 45 min of the experiment. *: GIN vs. AIN, $P<0.03$ at least. (E) Quantification of both extracellular bacteria after infection and in situ killed bacteria in GIN, AIN and human peripheral blood neutrophis (PBN). *: GIN vs. AIN or PBN, $P<0.003$ at least.

Innate immunity against bacterial infection develops during neutrophil differentiation. To compare this function between AIN and GIN, CD34+ cells were treated with G-CSF or Am80 for 6 days, followed by analyses of phagocytic and bacterial killing. Using the methodology described previously,[31,37] GIN, AIN, and PBN were incubated with log-phase *E. coli* at an MOI of 5 for 15 or 60 min, or use of *E. coli* in the absence of neutrophils to monitor bacterial growth. Both, the extracellular and recovered viable intracellular bacteria were quantified by CFU counts in samples where neutrophils were exposed to bacteria. The numbers of phagocytosed and killed bacteria were then calculated by subtracting extracellular bacteria only or both extracellular and intracellular bacteria, respectively, from the number of bacteria in the neutrophil-free condition. The extracellular bacteria were significantly decreased in both PBN and AIN samples (FIG. 4A, 4B). PBN rapidly killed bacteria within 15 min, while by 60 min there were only a few viable intracellular bacteria in either PBN or AIN samples (FIG. 4C). By contrast, GIN showed substantially impaired clearance of intracellular bacteria by 60 min of infection, retained higher level of extracellular bacteria, and was deficient in bacterial killing (FIG. 4A-D). To confirm that AIN possess greater bactericidal activity than do GIN, bacterial killing in situ was examined, using confocal microscopy of both viable bacteria labeled with SYTO9 fluorescent dye and killed bacteria labeled with propidium iodide (PI) fluorescent dye. The results demonstrated that significantly more surviving *E. coli* were retained in GIN samples, where we found much less dead bacteria in contrast to observations in AIN or PBN samples. Quantifying both extracellular bacteria after infection as well as in situ dead bacteria confirmed that both AIN and PBN possessed greater bactericidal activities than did GIN (FIG. 4E). Furthermore, ultrastructural images of *E. coli* infection by electron microscope showed that numerous intact/surviving bacteria were retained in GIN containing less dense vesicles; whereas similar to PBN, only a few intact/surviving bacteria were identified in AIN whose cytoplasm contained dense vesicles together with some primary- and secondary-like granules. Considered together, these data suggest that Am80-induced granulocytic differentiation is associated with enhanced neutrophil innate immunity against bacterial infection.

Example 3

Am80 Induces a Competitive Neutrophil Recovery Compared to G-CSF

Figure 7:
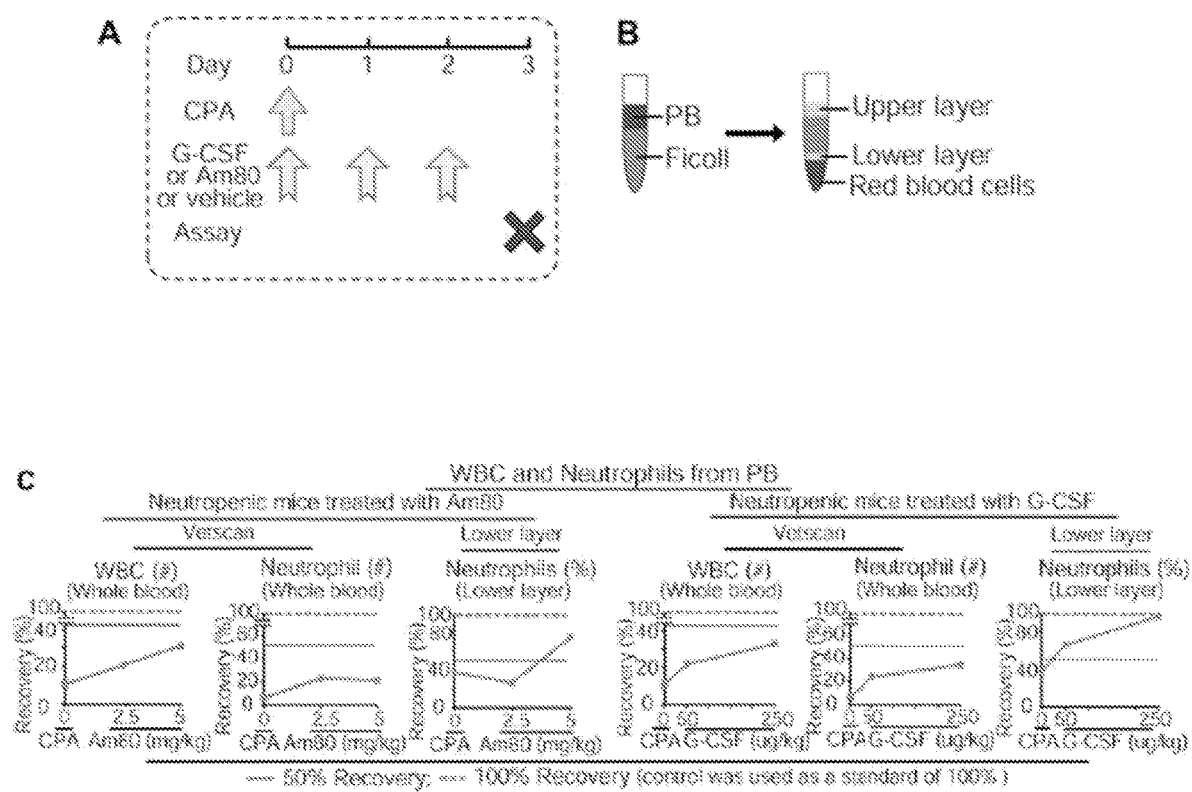
FIG. 7 depicts, in accordance with various embodiments of the present invention, that AM80 induces a competitive neutrophil recovery in neutropenic mice compared to those treated with G-CSF. (A) Illustration of the experimental design for analysis of neutrophil recovery measured at day 3 post-CPA administration with different doses of Am80 and G-CSF. (B) Peripheral blood (PB) was collected from euthanized control mice at day 3 and PB neutrophils were purified by using Ficoll-paque (1.084). (C) Analysis of white blood cells (WBC) and neutrophil recovery from neutropenic mice treated with different doses of Am80 or G-CSF at day 3.

Thirty C57BL6/J mice were randomly divided into six groups for the experiments. The experimental design for analysis of neutrophil recovery by using different dose of Am80 and G-CSF is illustrated in FIG. 7A. A single dose of intraperitoneal injection of cyclophosphamide (CPA) of 200 mg/kg was performed at day 0 to induce neutropenia. Am80 or G-CSF or vehicle was administrated after 4 hr of CPA injection for consecutive 3 days. Mouse neutropenia was induced 48-60 hr after CPA injection. Experiment was performed at day 3. Peripheral blood (PB) was collected from euthanized control mice at day 3 and PB neutrophils were purified by using Ficoll-paque (1.084). The majority of neutrophils were identified in the lower level of Ficoll paque, as reflected by granulocytic morphology analysis (FIG. 7B). Analysis of white blood cells (WBC) and neutrophil recovery from neutropenic mice treated with different doses of Am80 or G-CSF at day 3 is shown in FIG. 7C. Am80 of 5 mg/kg showed a competitive neutrophil recovery in the lower level of Ficoll-paque compared to G-CSF of 250 µg.

Example 4

Figure 8A:
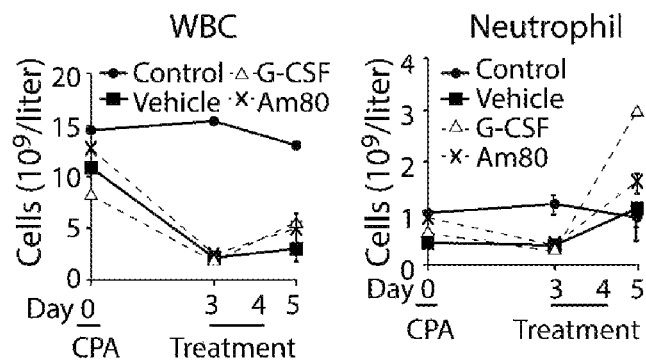
FIG. 8A-8G depict, in accordance with various embodiments of the present invention, that neutrophils mobilized by Am80 in neutropenic mice display greater bactericidal activity than those by G-CSF.
Figure 8B:
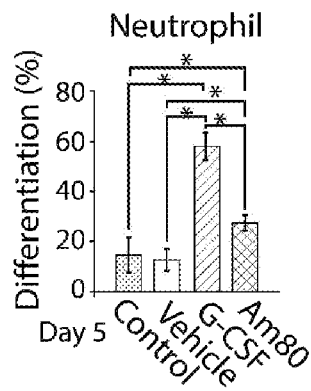
Figure 8C:
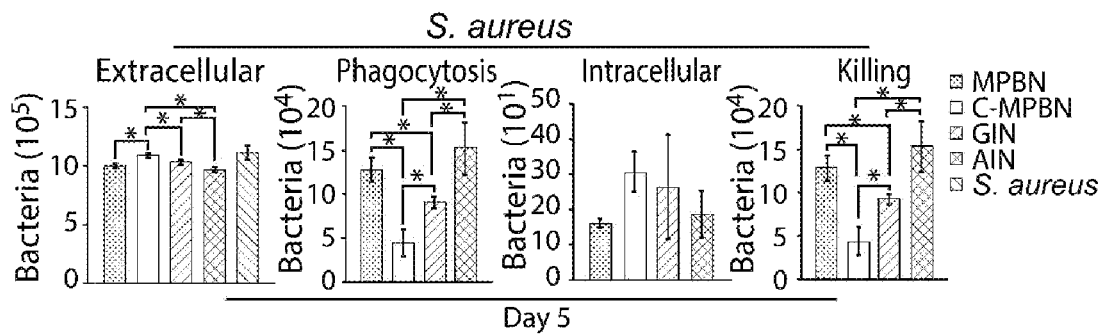
Figure 8D:
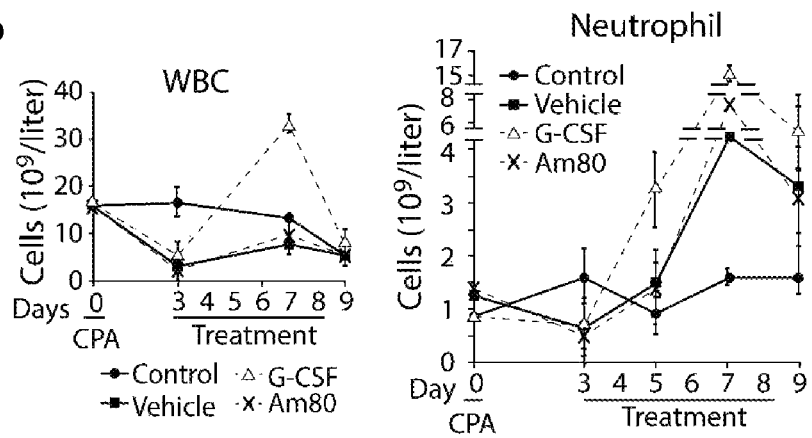
Figure 8E:
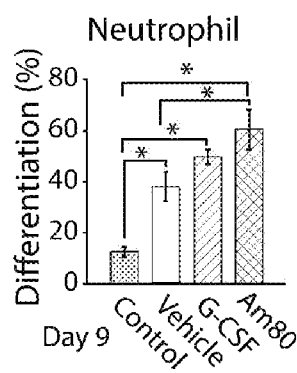
Figure 8F:
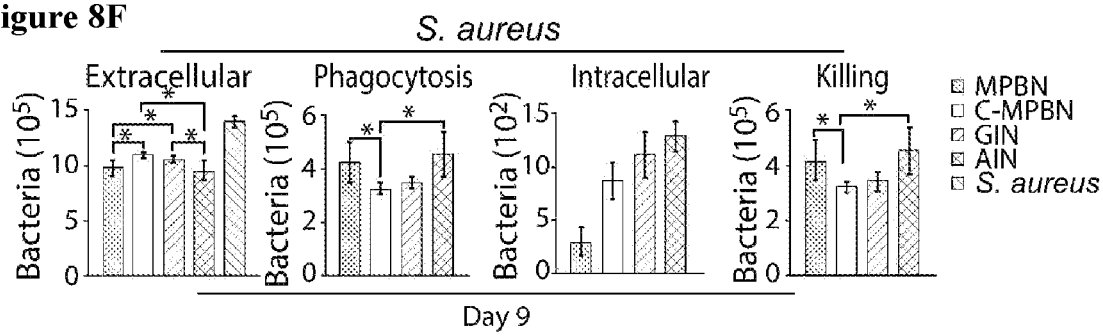

Neutrophils Mobilized by Am80 in Neutropenic Mice Display Greater Bactericidal Activity than those by G-CSF We found that a severe reduction of both WBCs and neutrophils occurred in all experimental mice 3 days after injection of CPA, compared with control mice (FIG. 8A). Rapidly thereafter at day 5 with injection of G-CSF or Am80 or vehicle for 2 consecutive days, a remarkably accelerated neutrophil recovery was induced by G-CSF compared with Am80, whereas neutrophil counts in vehicle group also returned nearly to control value (FIG. 8A-8B). These neutrophils were purified from PB of different groups of mice (20 mice in total), as shown by GIN sample, and used for analyzing of bactericidal activities against *S. aureus* infection in vitro. We found (FIG. 8C) that extracellular bacteria were eliminated significantly by either MPBNs, AINs, or GINS than neutrophils isolated from C-MPBNs treated with vehicle, whereas AINs were markedly more effective on eliminating bacteria than both GINS and C-MPBNs. Similar to MPBNs, AINs phagocytized and killed significantly more bacteria than either GINs or C-MPBNs. Because the accelerated neutrophil recovery ceased at day 7 (FIG. 8D), we purified neutrophils from PB of different mice at day 9 (FIG. 8E) to compare their bactericidal activities after cessation of accelerated neutrophil recovery. The results showed that both MPBNs and AINs still displayed significantly higher bactericidal activity than did C-MPBNs, whereas there was no difference in either phagocytosis or bacterial killing between GINs and C-MPBNs (FIG. 8F). These findings demonstrate that similar to MPBNs, neutrophils mobilized by Am80 in neutropenic mice are significantly more efficacious against *S aureus* infection than those by G-CSF, even though G-CSF can induce remarkably more neutrophils than do Am80 at earlier stage of neutrophil recovery. Moreover, although C-MPBN counts reach significantly higher level than control values at later stage of neutrophil recovery, the bactericidal activities of C-MPBNs are still significantly lower than MPBNs or AINs.

Figure 8G:
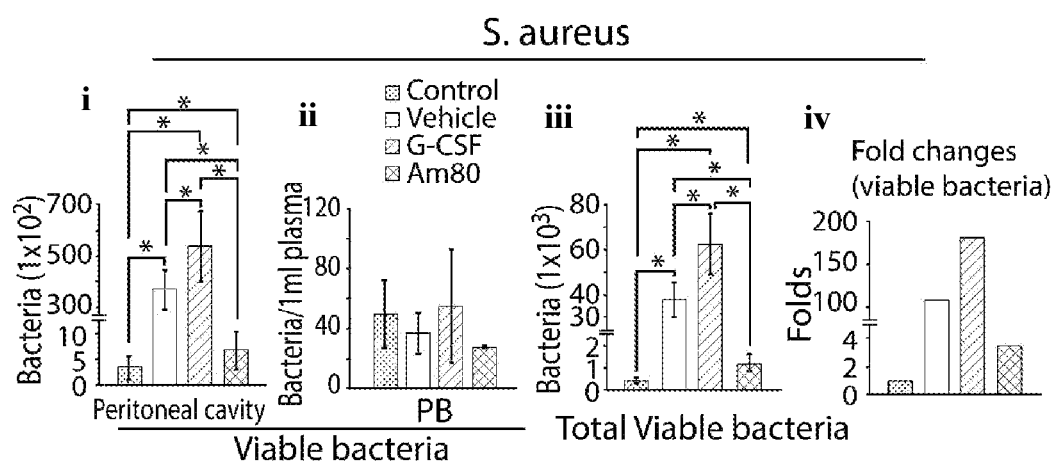

Using a neutropenic mouse model induced by a single dose of CPA, as described,[31,32] the inventors tested whether in vivo mobilized neutrophils by Am80 indeed possess the same greater neutrophil immunity against bacterial infection compared to those by G-CSF, as observed in the ex vivo model (FIG. 8A-8F). Twenty C57BL6/J mice were randomly divided into four groups for the in vivo experiments. CPA in the amount of 200 mg/Kg was administered at day 0. G-CSF, 250 μm/Kg or Am80, 5 mg/Kg were administered at days 0, 1 and 2. After 16 hr of intraperitoneal inoculation of $3 \times 10^7$ S. aureus in logarithmic growth phase, purified neutrophils were analyzed for their bactericidal activities by determining the numbers of viable extracellular bacteria in peritoneal cavity (FIG. 8G-i) and PB (FIG. 8G-ii). The numbers of viable bacteria were counted from 3 ml of PBS-washed peritoneal fluid as well as with an estimated 1.5 ml of total blood plasma. P value of viable bacteria in peritoneal cavity: Am80 vs. G-CSF, P <2.4 E-8; control vs. G-CSF, P<4.7 E-9; vehicle vs. G-CSF, P<8.3 E-3; Am80 vs. vehicle, P<3.1 E-9; Am80 vs. control, P<0.038. FIG. 8A-iii shows the total viable extracellular bacteria from FIGS. 8G-i and -ii. Am80 vs. G-CSF, P<1.9 E-6; control vs. G-CSF, P<9.4 E-9; vehicle vs. G-CSF, P<6.5 E-4; Am80 vs. vehicle, P<6.8 E-7; control vs. Am80, P<3.8 E-5. FIG. 8G-iv shows the fold changes in viable bacteria from FIG. 8G-iii. Viable bacteria in control group are used as a standard of 1 fold.

Using a neutropenic mouse model induced by a single dose of CPA, as described,[31,32] the inventors tested whether in vivo mobilized neutrophils by Am80 indeed possess the same—greater neutrophil immunity against bacterial infection compared to those by G-CSF, as observed in the in vivo model (FIG. 8A). We found that a severe reduction of both WBCs and neutrophils occurred in all experimental mice 3 days after injection of CPA, compared with control mice (FIG. 8B). Rapidly thereafter at day 5 with injection of G-CSF or Am80 or vehicle for 2 consecutive days, a remarkably accelerated neutrophil recovery was induced by G-CSF compared with Am80, whereas neutrophil counts in vehicle group also returned nearly to control value (FIG. 8B-8C). These neutrophils were purified from PB of different mice, as shown by GIN sample and used for analysis of bactericidal activities against S. aureus infection in vitro. We found (FIG. 8D) that extracellular bacteria were eliminated significantly by either MPBNs, AINs, or GINs than neutrophils isolated from C-MPBNs treated with vehicle, whereas AINs were markedly more effective on eliminating bacteria than both GINs and C-MPBNs. Similar to MPBNs, AINs phagocytized and killed significantly more bacteria than either GINs or C-MPBNs. Because the accelerated neutrophil recovery ceased at day 7 (FIG. 8E), we purified neutrophils from PB of different mice at day 9 (FIG. 8F) to compare their bactericidal activities after cessation of accelerated neutrophil recovery. The results showed that both MPBNs and AINs still displayed significantly higher bactericidal activity than did C-MPBNs, whereas there was no difference in either phagocytosis or bacterial killing between GINs and C-MPBNs (FIG. 8G). These findings demonstrate that similar to MPBNs, neutrophils mobilized by Am80 in neutropenic mice are significantly more efficacious against S aureus infection than those by G-CSF, even though G-CSF can induce remarkably more neutrophils than do Am80 at earlier stage of neutrophil recovery. Moreover, although C-MPBN counts reach significantly higher level than control values at later stage of neutrophil recovery, the bactericidal activities of C-MPBNs are still significantly lower than MPBNs or AINs.

The studies herein demonstrate that ex vivo and in-vivo-generated neutrophils by Am80 treatment of CD34+ cells not only exhibit greater differentiation maturity but also possess higher efficacy against bacterial infection than does G-CSF. This is likely through coordinating functional interaction of CD66 with CD18 to enhance the development of neutrophil innate immunity arising from granulopoiesis. Further determination of such regulatory mechanism should provide new insights into retinoid-mediated granulopoiesis and neutrophil differentiation. This will, in turn, provide compelling molecular basis for devising effective therapies against neutropenia as well as for ex vivo-generating granulocytes for transfusion therapy to reduce the duration of neutropenia, utilizing Am80 as a cost-effective therapeutic molecule.

REFERENCES

1. Huston A, Lyman G H. Agents under investigation for the treatment and prevention of neutropenia. Expert Opin Investig Drugs. 2007; 16:1831-1840.
2. Beekman R, Touw I P. G-CSF and its receptor in myeloid malignancy. Blood. 2010; 115:5131-5136.
3. Kuderer N M, Dale D C, Crawford J, Cosler L E, Lyman G H. Mortality, morbidity, and cost associated with febrile neutropenia in adult cancer patients. Cancer. 2006; 106: 2258-2266.
4. Marti F M, Cullen M H, Roila F. Management of febrile neutropenia: ESMO clinical recommendations. Ann Oncol. 2009; 20 Suppl 4:166-169.
5. Dick E P, Prince L R, Sabroe I. Ex vivo-expanded bone marrow CD34+ derived neutrophils have limited bactericidal ability. Stem Cells. 2008; 26:2552-2563.
6. Kagechika H. Novel synthetic retinoids and separation of the pleiotropic retinoidal activities. Curr Med Chem. 2002; 9:591-608.
7. Miwako I, Kagechika H. Tamibarotene. Drugs Today (Barc). 2007; 43:563-568.
8. Ohnishi K. PML-RARalpha inhibitors (ATRA, tamibaroten, arsenic troxide) for acute promyelocytic leukemia. Int J Clin Oncol. 2007; 12:313-317.
9. Fukasawa H, Iijima T, Kagechika H, Hashimoto Y, Shudo K. Expression of the ligand-binding domain-containing region of retinoic acid receptors alpha, beta and gamma in *Escherichia coli* and evaluation of ligand-binding selectivity. Biol Pharm Bull. 1993; 16:343-348.
10. Hashimoto Y, Kagechika H, Shudo K. Expression of retinoic acid receptor genes and the ligand-binding selectivity of retinoic acid receptors (RAR's). Biochem Biophys Res Commun. 1990; 166:1300-1307.
11. de The H, Marchio A, Tiollais P, Dejean A. Differential expression and ligand regulation of the retinoic acid receptor alpha and beta genes. Embo J. 1989; 8:429-433.
12. Chambon P. A decade of molecular biology of retinoic acid receptors. Faseb J. 1996; 10:940-954.
13. Evans T. Regulation of hematopoiesis by retinoid signaling. Exp Hematol. 2005; 33:1055-1061.
14. Douer D, Ramezani L, Parker J, Levine A M. All-transretinoic acid effects the growth, differentiation and apoptosis of normal human myeloid progenitors derived from purified CD34+ bone marrow cells. Leukemia. 2000; 14:874-881.
15. Wang J, Barsky L W, Shum C H, et al. Retinoid-induced G1 arrest and differentiation activation are associated with a switch to cyclin-dependent kinase-activating kinase hypophosphorylation of retinoic acid receptor alpha. Journal of Biological Chemistry. 2002; 277:43369-43376.
16. Wang J G, Barsky L W, Davicioni E, et al. Retinoic acid induces leukemia cell G1 arrest and transition into differentiation by inhibiting cyclin-dependent kinase-activating kinase binding and phosphorylation of PML/ RARalpha. Faseb J. 2006; 20:2142-2144.
17. Luo P, Wang A, Payne K J, et al. Intrinsic retinoic acid receptor alpha-cyclin-dependent kinase-activating kinase signaling involves coordination of the restricted proliferation and granulocytic differentiation of human hematopoietic stem cells. Stem Cells. 2007; 25:2628-2637.
18. Gudas L J. Emerging roles for retinoids in regeneration and differentiation in normal and disease states. Biochim Biophys Acta. 2012; 1821:213-221.
19. Soprano D R, Qin P, Soprano K J. Retinoic acid receptors and cancers. Annu Rev Nutr. 2004; 24:201-221.
20. Melnick A, Licht J D. Deconstructing a disease: RARalpha, its fusion partners, and their roles in the pathogenesis of acute promyelocytic leukemia. Blood. 1999; 93:3167-3215.
21. Collins S J. Retinoic acid receptors, hematopoiesis and leukemogenesis. Curr Opin Hematol. 2008; 15:346-351.
22. Cornic M, Delva L, Castaigne S, et al. In vitro all-trans retinoic acid (ATRA) sensitivity and cellular retinoic acid binding protein (CRABP) levels in relapse leukemic cells after remission induction by ATRA in acute promyelocytic leukemia. Leukemia. 1994; 8 Suppl 2:S16-19.
23. Degos L, Dombret H, Chomienne C, et al. All-trans-retinoic acid as a differentiating agent in the treatment of acute promyelocytic leukemia. Blood. 1995; 85:2643-2653.
24. Delva L, Cornic M, Balitrand N, et al. Resistance to all-trans retinoic acid (ATRA) therapy in relapsing acute promyelocytic leukemia: study of in vitro ATRA sensitivity and cellular retinoic acid binding protein levels in leukemic cells. Blood. 1993; 82:2175-2181.
25. Ishida S, Shigemoto-Mogami Y, Shinozaki Y, et al. Differential modulation of PI3-kinase/Akt pathway during all-trans retinoic acid- and Am80-induced HL-60 cell differentiation revealed by DNA microarray analysis. Biochem Pharmacol. 2004; 68:2177-2186.
26. Jimi S, Mashima K, Matsumoto T, Hara S, Suzumiya J, Tamura K. RARalpha is a regulatory factor for Am-80-induced cell growth inhibition of hematologic malignant cells. Int J Oncol. 2007; 31:397-404.
27. Hashimoto Y, Kagechika H, Kawachi E, Fukasawa H, Saito G, Shudo K. Correlation of differentiation-inducing activity of retinoids on human leukemia cell lines HL-60 and NB4. J Cancer Res Clin Oncol. 1995; 121:696-698.
28. Tobita T, Takeshita A, Kitamura K, et al. Treatment with a new synthetic retinoid, Am80, of acute promyelocytic leukemia relapsed from complete remission induced by all-trans retinoic acid. Blood. 1997; 90:967-973.
29. Chaudhry P, Yang X, Wagner M, Jong A Y, Wu L. Retinoid-regulated FGF8f secretion by osteoblasts bypasses retinoid stimuli to mediate granulocytic differentiation of myeloid leukemia cells. Mol Cancer Ther. 2012; 11:267-276.
30. Mittal R, Krishnan S, Gonzalez-Gomez I, Prasadarao N V. Deciphering the roles of outer membrane protein A extracellular loops in the pathogenesis of *Escherichia coli* K1 meningitis. J Biol Chem. 2011; 286:2183-2193.
31. Mittal R, Bulgheresi S, Emami C, Prasadarao N V. *Enterobacter sakazakii* targets DC-SIGN to induce immunosuppressive responses in dendritic cells by modulating MAPKs. J Immunol. 2009; 183:6588-6599.
32. Hager M, Cowland J B, Borregaard N. Neutrophil granules in health and disease. J Intern Med. 2010; 268:25-34.
33. Borregaard N, Sorensen O E, Theilgaard-Monch K. Neutrophil granules: a library of innate immunity proteins. Trends Immunol. 2007; 28:340-345.
34. van der Velden W J, Blijlevens N M, Donnelly J P. The potential role of lactoferrin and derivatives in the management of infectious and inflammatory complications of hematology patients receiving a hematopoietic stem cell transplantation. Transpl Infect Dis. 2008; 10:80-89.
35. Ward P P, Paz E, Conneely O M. Multifunctional roles of lactoferrin: a critical overview. Cell Mol Life Sci. 2005; 62:2540-2548.
36. Kerr M A, Stocks S C. The role of CD15-(Le(X))-related carbohydrates in neutrophil adhesion. Histochem J. 1992; 24:811-826.
37. Mittal R, Prasadarao N V. Outer membrane protein A expression in *Escherichia coli* K1 is required to prevent the maturation of myeloid dendritic cells and the induction of IL-10 and TGF-beta. J Immunol. 2008; 181:2672-2682.
38. Groves E, Dart A E, Covarelli V, Caron E. Molecular mechanisms of phagocytic uptake in mammalian cells. Cell Mol Life Sci. 2008; 65:1957-1976.
39. Kuespert K, Pils S, Hauck C R. CEACAMs: their role in physiology and pathophysiology. Curr Opin Cell Biol. 2006; 18:565-571.
40. Kuijpers T W, van der Schoot C E, Hoogerwerf M, Roos D. Cross-linking of the carcinoembryonic antigen-like glycoproteins CD66 and CD67 induces neutrophil aggregation. J Immunol. 1993; 151:4934-4940.
41. Lo S K, Lee S, Ramos R A, et al. Endothelial-leukocyte adhesion molecule 1 stimulates the adhesive activity of leukocyte integrin CR3 (CD11b/CD18, Mac-1, alpha m beta 2) on human neutrophils. J Exp Med. 1991; 173: 1493-1500.
42. Skubitz K M, Campbell K D, Skubitz A P. CD66a, CD66b, CD66c, and CD66d each independently stimulate neutrophils. J Leukoc Biol. 1996; 60:106-117.
43. Ando K, Muguruma Y, Yahata T. Humanizing bone marrow in immune-deficient mice. Curr Top Microbiol Immunol. 2008; 324:77-86.
44. Mayack S R, Wagers A J. Osteolineage niche cells initiate hematopoietic stem cell mobilization. Blood. 2008; 112:519-531.
45. Kuijpers T W, Hoogerwerf M, van der Laan L J, et al. CD66 nonspecific cross-reacting antigens are involved in neutrophil adherence to cytokine-activated endothelial cells. J Cell Biol. 1992; 118:457-466.
46. Park D J, Chumakov A M, Vuong P T, et al. CCAAT/ enhancer binding protein epsilon is a potential retinoid target gene in acute promyelocytic leukemia treatment. J Clin Invest. 1999; 103:1399-1408.
47. Bush T S, St Coeur M, Resendes K K, Rosmarin A G. GA-binding protein (GABP) and Sp1 are required, along with retinoid receptors, to mediate retinoic acid responsiveness of CD18 (beta 2 leukocyte integrin): a novel mechanism of transcriptional regulation in myeloid cells. Blood. 2003; 101:311-317.
48. Hickstein D D, Baker D M, Gollahon K A, Back A L. Identification of the promoter of the myelomonocytic leukocyte integrin CD11b. Proc Natl Acad Sci USA. 1992; 89:2105-2109.
49. Chih D Y, Chumakov A M, Park D J, Silla A G, Koeffler H P. Modulation of mRNA expression of a novel human myeloid-selective CCAAT/enhancer binding protein gene (C/EBP epsilon). Blood. 1997; 90:2987-2994.

50. Faurschou M, Borregaard N. Neutrophil granules and secretory vesicles in inflammation. Microbes Infect. 2003; 5:1317-1327.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for treating, inhibiting, reducing the severity of or promoting prophylaxis of neutropenia in a subject in need thereof, comprising:
    selecting a subject having congenital neutropenia, neutropenia due to destruction of neutrophils by pathogen infection, or neutropenia due to hemodialysis, malaria, systemic lupus erythematosus, aplastic anemia, vitamin deficiency, folic acid deficiency or a combination thereof, or the subject undergoing chemotherapy or having been administered with a therapeutic agent that affects bone marrow and results in reduction of neutrophils; and
    administering a therapeutically effective amount of tamibarotene at 0.005 mg orally/kg per day to 0.150 mg orally/kg per day to the subject so as to treat, inhibit, reduce the severity of or promote prophylaxis against said neutropenia,
    wherein tamibarotene increases the population of functional neutrophils in the subject and the said neutrophils possess microbicidal activity.

2. The method of claim 1, wherein the method is for treating neutropenia and the method comprises
    selecting a subject undergoing chemotherapy prior to administering the therapeutically effective amount of tamibarotene thereby treating the neutropenia in the subject.

3. The method of claim 2, further comprising administering a chemotherapeutic agent.

4. The method of claim 3, wherein the chemotherapeutic agent and the tamibarotene are administered concurrently or sequentially.

5. A method for treating pathogen infection that leads to destruction of neutrophils in a subject in need thereof comprising:
    selecting a subject with pathogen infection that leads to destruction of neutrophils; and administering a therapeutically effective amount of tamibarotene at 0.005 mg orally/kg per day to 0.15 mg orally/kg per day and an anti-microbial agent to the subject to treat the pathogen infection in the subject, wherein tamibarotene increases the population of functional neutrophils in the subject and the neutrophils possess microbicidal activity, thereby treating the pathogen infection in the subject.

6. The method of claim 5, wherein the tamibarotene and the anti-microbial agent are administered concurrently or sequentially.

7. The method of claim 1, wherein the subject is human.

8. The method of claim 5, wherein the subject is human.

9. The method of claim 1 or 5, wherein the therapeutically effective amount of tamibarotene is 0.01 to 0.05 mg orally/kg/day or 0.05-0.1 mg orally/kg/day.

10. The method of claim 1 or 5, wherein the neutrophils express CD66 and CD18.

11. The method of claim 1, wherein the neutropenia is congenital neutropenia.

12. The method of claim 1, wherein the therapeutic agent that affects bone marrow and results in reduction of neutrophils comprises sulfonamide, cyclophosphamide, flecainide, phenytoin, indomethacin, propylthiouracil, carbimazole, chlorpromazine, trimethoprim, sulfamethoxazole, clozapine, ticlodipine, or a combination thereof.

13. A method for treating, inhibiting, reducing the severity of or promoting prophylaxis of neutropenia in a subject in need thereof, comprising:

selecting a subject having congenital neutropenia, neutropenia due to destruction of neutrophils by pathogen infection, or neutropenia due to hemodialysis, malaria, systemic lupus erythematosus, aplastic anemia, vitamin deficiency, folic acid deficiency or a combination thereof, or the subject undergoing chemotherapy or having been administered with a therapeutic agent that affects bone marrow and results in reduction of neutrophils; and administering to the subject a pharmaceutical composition comprising a pharmaceutically acceptable excipient and a therapeutically effective amount of tamibarotene for increasing the population of microbicidal neutrophils, and wherein the tamibarotene is administered intravenously, intramuscularly, intraperitoneally, or via inhalation.

14. The method of claim 13, wherein the tamibarotene is administered intravenously or via inhalation.

15. The method of claim 13, wherein the tamibarotene is administered intramuscularly.

16. The method of claim 13, wherein the tamibarotene is administered intraperitoneally.

* * * * *